United States Patent [19]

Deschamps et al.

[11] Patent Number: 4,536,594

[45] Date of Patent: Aug. 20, 1985

[54] PROCESS FOR THE PREPARATION OF BETA-DISUBSTITUTED MONOCARBOXYLIC ACIDS

[75] Inventors: Patrice P. M. Deschamps, Aix en Provence; Roger Gallo, Bouc Bel Air; Henri Grangette, Lyons, all of France

[73] Assignee: Elf France, Paris, France

[21] Appl. No.: 540,118

[22] Filed: Oct. 7, 1983

[30] Foreign Application Priority Data

Oct. 8, 1982 [FR] France ................................ 82 16907

[51] Int. Cl.$^3$ .................... C07C 51/00; C07C 53/126; C07C 53/132; C07C 53/134
[52] U.S. Cl. .................................... 562/400; 260/413; 562/500; 562/501; 562/502; 562/504; 562/606
[58] Field of Search ............... 562/504, 606, 400, 500, 562/501, 502; 260/413 HC

[56] References Cited

U.S. PATENT DOCUMENTS 2,370,494  2/1945  Schmerling ...................... 562/606
3,637,821  1/1972  Bott ................................... 562/504

Primary Examiner—J. E. Evans
Attorney, Agent, or Firm—Burgess, Ryan & Wayne

[57] ABSTRACT

A process for the preparation of beta-disubstituted monocarboxylic acids derived from tertiary acyclic, monocyclic or bicyclic hydrocarbons. The process consists in reacting said hydrocarbons with vinylidene chloride and either a functional compound where the molecule includes a tertiary carbon atom bonded to the heteroatom of a functional group such as a tertiary alcohol, an ether, or a tertiary halide or an alkene, in the presence of a concentrated protonic acid. The reaction can be carried out in the presence of a catalyst of the Lewis acid type and particularly $BF_3$. These acids are useful as synthesis intermediates and as additives for oils and lubricants.

13 Claims, No Drawings

PROCESS FOR THE PREPARATION OF BETA-DISUBSTITUTED MONOCARBOXYLIC ACIDS

BACKGROUND OF THE INVENTION

The present invention relates to a process for the preparation of beta-disubstituted monocarboxylic acids derived from acyclic, monocyclic, or bicyclic hydrocarbons.

These acids are useful as synthesis intermediates and as additives for oils and lubricants. Therefore, it is important to find a simple method of synthesis using an economic raw material. Thus, the interest of using petroleum fractions rich in isoparaffins for the synthesis of these acids is evident.

The synthesis of beta-disubstituted monocarboxylic acids by reacting a tertiary functional compound such as an alcohol, tertiary ether or halide, or an alkene with vinylidene chloride in a concentrated sulfuric acid medium and in the presence of $BF_3$ followed by the hydrolysis of the reaction mixture by water is known (K. BOTT, H. HELLMAN, ANGEW. Chem 78 932 (1966)).

 

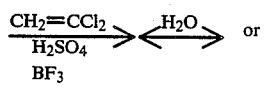

 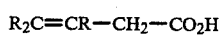

It is likewise known that adamantane, a polycyclic compound, reacts with vinylidene chloride according to the process described in the prior art. This very rigid structure has the peculiarity of reacting with vinylidene chloride to form a diacid, the 1,3, dicarboxymethyladamantane (U.S. Pat. No. 3,751,455).

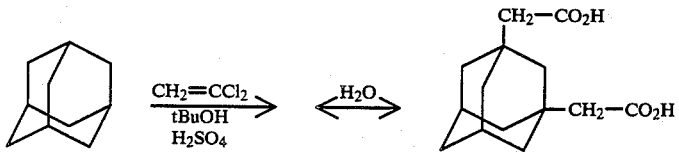

This method makes use of a Lewis-acid type catalyst and specially of $BF_3$, the use of which is complicated. An improvement on the preceding method has been proposed by A. NILSON and R. CARLSON (Acta. Chem. Scand. 1980 621) who have carried out the synthesis not in the presence of gaseous $BF_3$ but of a soluble $BF_3$ hydrate, but without eliminating the presence of $BF_3$.

However, the main objection to this synthesis is that it cannot be applied to tertiary acyclic, monocyclic, or bicyclic hydrocarbons such as isoparaffins of petroleum origin.

In fact, the acyclic, monocyclic, or bicyclic tertiary hydrocarbons do not react with vinylidene chloride in a concentrated protonic acid medium even in the presence of a Lewis-acid type catalyst such as $BF_3$.

BRIEF DESCRIPTION OF THE INVENTION

This invention makes it possible to overcome this deficiency and to carry out the synthesis of beta-disubstituted monocarboxylic acids of the general formula:

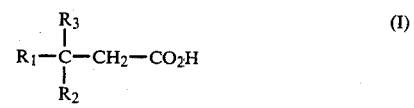

wherein $R_1$, $R_2$, and $R_3$ are identical or different and represent each a saturated or unsaturated monovalent hydrocarbon radical containing from 1 to 22, preferably 1 to 12 carbon atoms, or $R_1$ and $R_2$ can be interbonded to form with the carbon atoms to which they are attached a monocyclic or bicyclic structure comprising from 5 to 22, preferably from 5 to 12 carbon atoms, starting from tertiary hydrocarbons of the general formula

wherein $R_1$, $R_2$ and $R_3$ have the above meaning.

It has in effect been discovered that by reacting an acyclic, monocyclic, or bicyclic hydrocarbon of the general formula II mixed with vinylidene chloride and either a functional compound wherein the molecule includes a tertiary carbon atom bonded to a heteroatom of a functional group such as a tertiary alcohol, a tertiary ether, or a tertiary halide or an alkene in the presence of a concentrated protonic acid, there is obtained a mixture of two beta-disubstituted carboxylic acids, one derived from hydrocarbon and the other from the functional compound.

DETAILED DESCRIPTION OF THE INVENTION

The functional compounds that can be used for this reaction have the general formula

wherein $R_4$, $R_5$, $R_6$ are identical or different and represent each a saturated or unsaturated monovalent hydrocarbon radical containing from 1 to 22, preferably from 1 to 12 carbon atoms, or $R_4$ and $R_5$ can be interbonded to form with the carbon atom to which they are attached, a monocyclic or bicyclic structure comprising from 5 to 22, and preferably from 5 to 12, carbon atoms and Y is a functional group such as OH, OR, or halide where R is a monovalent hydrocarbon radical having 1 to 8, preferably 1 to 4, carbon atoms.

The alkene that can be used for this reaction has the general formula:

(IV)

wherein $R_7$, $R_8$, $R_9$ are identical or different and each represents a saturated or unsaturated monovalent hydrocarbon radical containing from 1 to 22, preferably from 1 to 12, carbon atoms.

In the course of the reaction, the functional compound or the alkene produces a primary carbocation capable of generating by transfer a carbocation on the tertiary carbon of the hydrocarbon. There is thus obtained a carboxylic acid of formula V, or VI, derived from the primary carbocation, that is, from the functional derivative III, or the alkene of the formula IV, and a carboxylic acid of formula (I) derived from the carbocation formed by transfer, that is, from the hydrocarbon of formula II.

boxymethyl-1-cyclopentane and methyl-1-caboxymethyl-1-cyclohexane.

The temperature at which the reaction is carried out is generally between 0° and 40 ° C., and preferably between 5° and 20° C. In most cases, it is not necessary to go above a temperature of about 15° C.

Although it is generally not necessary to operate under pressure, it may be advantageous to carry out the reaction under autogenic pressure when one of the reagents is gaseous.

The reaction medium comprises a concentrated protonic acid, preferably sulfuric acid having a concentration of more than 90% by weight. It is possible to effect the reaction in the presence of a Lewis-acid type catalyst, and especially $BF_3$.

The respective quantities of vinylidene chloride, hydrocarbon and functional derivatives may vary within wide ranges, but it is preferable to operate with an excess of vinylidene chloride and of hydrocarbon in relation to the functional derivative. It is preferable to use 1.1 to 2 moles vinylidene chloride and 1.1 to 3 moles of alkene per mole of functional derivative.

The process according to the invention can be carried out using different methods for bringing the reagents into contact. For example, it is possible to introduce a mixture of a functional derivative or of an alkene with vinylidene chloride into a mixture of sulfuric acid and alkane, the temperature of the reaction medium being kept at the selected value.

The carboxylic acids obtained by the process according to the invention can be separated from the reaction medium by any known method. For example, if the

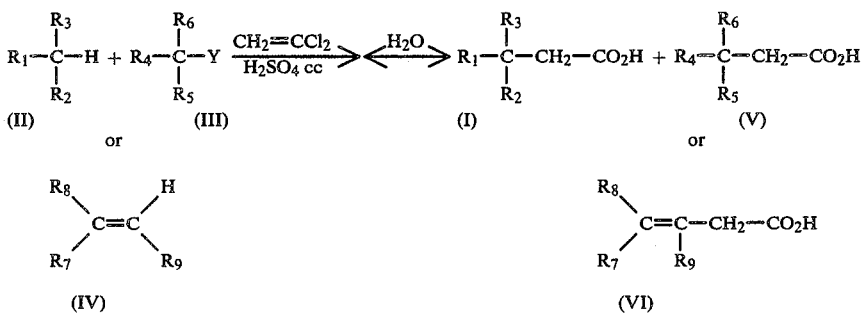

reaction mixture has been treated with water, the acids may be collected with the organic phase and distilled. It is also possible after the water treatment to separate the acids by converting them to the potassium salt thereof, regeneration of the free acid in the presence of concentrated HCl being followed by an extraction and a distillation.

The examples that follow illustrate the invention without limiting it.

EXAMPLE 1

120 ml of 96% sulfuric acid and 0.50 mole (49.1 g) of methylcyclohexane were poured into a 500 ml reactor provided with a coolant, a dropping funnel, a thermometer and mechanical stirring means. The reactor was cooled to 10° C. and there was added by means of a dropping funnel a mixture of 0.25 mole (18.5 g) tertiary butanol and 0.375 mole (36.3 g) vinylidene chloride over a period of 1 hour and 30 minutes. At the end of the addition, the stirring was continued for 2 hours, 30 minutes. There was observed in the course of the reac- Among the tertiary hydrocarbons of the general formula II there are included the acyclic hydrocarbons such as isobutane, isopentane, 2-methylpentane; monocyclic hydrocarbons such as methylcyclopentane, methylcyclohexane, and bicyclic hydrocarbons such as methyldecalines and methylindanes.

It is also possible to use petroleum fractions containing one or more of the above mentioned hydrocarbons.

Particularly useful functional derivatives of the general formula III are the tertiary alcohols such as tert-butanol, isopentanol, isohexanol, methyl-1-cyclohexanol, methyl-1-cyclopentanol; ethers such as methyl-tertbutylether (MTBE) and tertamylether (TAME) and the tertiary alkyl halides such as tertbutyl chloride and tertamyl chloride.

As examples of useful alkenes there are included isobutene, isopentene, methylpentenes, or petroleum fractions containing these alkenes.

Among the beta-substituted carboxylic acids that can be prepared according to the invention, there can be mentioned dimethyl-3,3-butyric acid, dimethyl-3,3-pentanoic acid, dimethyl-3,3-hexanoic acid, methyl-1-cartion a gaseous mixture of hydrochloric acid and isobutane. The reaction mixture was then treated with 400 g crushed ice. The aqueous phase was washed twice with 100 ml portions of hexane. The different organic phases were combined and treated with a 2N potash solution until the pH of the aqueous phase was in the range of 9-10. The basic aqueous phase was reacidified with concentrated HCl to a pH 1. The carboxylic acids were extracted twice with 100 ml portions of benzene. The benzene phases were combined and washed with 50 ml water. After decantation, the benzene was evaporated. The remaining fraction of 17.1 g, comprises a mixture of direct acid (dimethyl-3,3-butanoic) and transfer acid (methyl-1-carboxymethyl-1-cyclohexane). The molar yield of carboxylic acids in relation to tertiary butanol is 52% with a selectivity of 61% of direct acid (dimethyl-3,3-butanoic) and 39% of transfer acid (methyl-1-carboxymethyl -1-cyclohexane).

EXAMPLE 2

100 ml of 96% sulfuric acid and 0.75 mole (54.1 g) isopentane were charged into a 500 ml reactor equipped as in the preceding example. There was added by means of a dropping funnel a mixture of 0.25 mole (23.1 g) tertbutyl chloride and 0.25 mole (24.2 g) vinylidene chloride in 1 hour, 15 minutes, then 0.124 mole (12.1 g) vinylidene chloride was added in 30 minutes, the temperature of the mixture in the reactor was kept between 10° and 15° C. Stirring of the reactin mixture was continued for 2 hours after the addition at this temperature. The reaction mixture was then hydrolyzed with crushed ice and the acid fraction was obtained by extraction with hexane, treatment with KOH, separation by concentrated HCl, extraction with benzene and distillation. The molar yield of the carboxylic acid fraction, calculated in relation to the tertiary butyl chloride, was 63%; with a selectivity of 44% of direct acid (dimethyl-3,3-butanoic) and 56% of transfer acid (dimethyl-3,3-pentanoic).

EXAMPLE 3

120 ml of 96% sulfuric acid and 0.50 mole (42.1 g) methylcyclopentane were poured into a 500 ml reactor equipped as in the preceding example. There was added by means of a dropping funnel, a mixture of 0.25 mole (23.1 g) tert-butyl chloride and 0.25 mole (24.2 g) vinylidene chloride, the temperature of the mixture in the reactor was kept between 10° and 15° C.; then 0.125 mole (12.1 g) vinylidene chloride were added in 30 minutes. Stirring of the reaction mixture was continued for 2 hours at a temperature of 10°-15° C. The reaction mixture was then treated as in the preceding example. The molar yield of the carboxylic acid fraction, calculated in relation to the tert-butyl chloride, was 42% with a selectivity of 43% of direct acid (dimethyl-3,3-butanoic) and 57% of transfer acid (methyl-1-carboxymethyl-1-cyclopentane).

EXAMPLE 4

120 ml of 96% sulfuric acid and 0.75 mole (64.5 g) methyl-2-pentane was poured in the installation equipped as in the preceding example and following the same method of operation. There were added 0.25 mole (18.5 g) tertbutanol and 0.25 mole 929.2 g) vinylidene chloride over a period of 1 hour, 15 minutes, then 0.125 mole (12.1 g) of vinylidene chloride was added in 30 minutes. The temperature of the mixture in the reactor was maintained between 10° and 15° C. Stirring was continued for an additional 2 hours at the same temperature and the reaction mixture was treated as in the preceding example. The molar yield of the carboxylic acid fraction, calculated in relation to the tertbutanol, was 41% with a selectivity of 60% of direct acid (dimethyl-3,3-butanoic) and of 40% of transfer acid (dimethyl-3,3-hexanoic). Under the same operating conditions but in the absence of tert-butanol, 3,3-dimethyl-hexanoic acid is not obtained.

What is claimed is:

1. A process for the preparation of a beta-disubstituted monocarboxylic acid of the formula

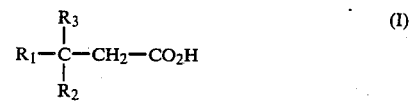

wherein $R_1$, $R_2$, and $R_3$ are identical or different and each represents a saturated or unsaturated monovalent hydrocarbon radical containing from 1 to 22 carbon atoms or $R_1$ and $R_2$ are interbonded to form with the carbon atoms to which they are attached a monocyclic or bicyclic structure comprising from 5 to 22 carbon atoms which comprises reacting a hydrocarbon of the formula

wherein $R_1$, $R_2$ and $R_3$ have the above meaning, with vinylidene chloride, and a functional compound wherein the molecule contains a tertiary carbon atom bonded to the heteroatom of a functional group or an alkene in the presence of a concentrated protonic acid.

2. A process according to claim 1, wherein a hydrocarbon of the formula

wherein $R_1$, $R_2$, $R_3$ are identical or different and each represents a saturated or unsaturated monovalent hydrocarbon radical containing from 1 to 12 carbon atoms or $R_1$ and $R_2$ are interbonded to form with the carbon atoms to which they are attached a monocyclic or bicyclic structure comprising from 5 to 12 carbon atoms.

3. A process according to claim 1, wherein the hydrocarbon of the formula II comprises a petroleum fraction containing at least one hydrocarbon of the formula II.

4. A process according to claim 1, wherein the functional compound has the formula

wherein $R_4$, $R_5$ and $R_6$ are identical or different and each represents a saturated or unsaturated monovalent hydrocarbon radical containing from 1 to 22 carbon atoms, or $R_4$ and $R_5$ are interbonded to form with the carbon atom to which they are attached a monocyclic or bicyclic structure comprising from 5 to 22 carbon atoms and Y is a functional group including OH, OR and halide, where R is a monovalent hydrocarbon radical having from 1 to 8 carbon atoms.

5. A process according to claim 1, which comprises reacting an alkene of the formula

wherein $R_7$, $R_8$, and $R_9$ are identical or different and each represents a saturated or unsaturated monovalent hydrocarbon radical containing from 1 to 22 carbon atoms.

6. A process according to claim 1, wherein the alkene comprises a petroleum fraction containing one or more alkenes of the formula IV.

7. A process according to claim 1, wherein the concentrated protonic acid is sulfuric acid in a concentration of more than 90% by weight.

8. A process according to claim 1, wherein the reaction is carried out in the presence of a Lewis-acid type catalyst.

9. A process according to claim 1, wherein from 1.1 to 2 moles of vinylidene chloride and from 1.1 to 3 moles of tertiary hydrocarbon are used per mole of functional compound in the reaction mixture.

10. A process according to claim 1, wherein the reaction is carried out at a temperature between 0° to 40° C.

11. A process according to claim 10, wherein the temperature is between about 5° and 20° C.

12. The process of claim 8, wherein the Lewis acid is $BF_3$.

13. The process according to claim 4, wherein the interbonded structure formed by $R_4$ and $R_5$ and the carbon atom to which they are attached comprises from 5 to 12 carbon atoms.

* * * * *